United States Patent [19]

Linowski et al.

[11] Patent Number: 5,721,613
[45] Date of Patent: Feb. 24, 1998

[54] FLUORESCENCE SPECTROMETER

[75] Inventors: Clemens Linowski; Thomas Doerr, both of Waldbronn, Germany

[73] Assignee: Hewlett Packard Company, Palo Alto, Calif.

[21] Appl. No.: 755,931

[22] Filed: Nov. 25, 1996

Related U.S. Application Data

[63] Continuation-in-part of Ser. No. 390,853, Feb. 17, 1995, abandoned.

[30] Foreign Application Priority Data

Mar. 21, 1994 [EP] European Pat. Off. ............ 94104392

[51] Int. Cl.⁶ ........................... G01J 3/443; G01N 21/64
[52] U.S. Cl. .................................. 356/318; 250/461.1
[58] Field of Search .................................. 356/317, 318; 250/458.1, 459.1, 461.1, 461.2; 350/317, 318

[56] References Cited

U.S. PATENT DOCUMENTS

| Re. 32,598 | 2/1988 | White | 356/318 |
|---|---|---|---|
| 5,196,709 | 3/1993 | Berndt et al. | 250/458.1 |
| 5,212,386 | 5/1993 | Gratton et al. | 356/317 |
| 5,303,026 | 4/1994 | Strobl et al. | 356/318 |
| 5,439,578 | 8/1995 | Dovichi et al. | 356/318 |
| 5,442,438 | 8/1995 | Batchelder et al. | 356/326 |

FOREIGN PATENT DOCUMENTS

| 217 024 A1 | 2/1982 | German Dem. Rep. |
| 213 512 | 1/1983 | German Dem. Rep. |
| 229 220 A1 | 11/1984 | German Dem. Rep. |
| 2 231 958 | 11/1990 | United Kingdom |

OTHER PUBLICATIONS

"Scintillation Detectors Using Large Area Silicon Avalanche Photodiodes", G. Entine et al., IEEE Transactions on Nuclear Science. vol. NS-30 (1983), No. 1.

"Unintensified Photodiode Array Fluorescence Detector for High-Performance Liquid Chromatography", Jeff Wegrzyn et al., Anal. Chem. 1990, vol. 62, pp. 1754-1758.

"Photoluminescence Lifetime Microscope Spectrometer Based On Time-Correlated Single-Photon Counting With an Avalanche Diode Detector", T.A. Louis, Rev. Sci. Instrum. 61, Jan. 1990, pp. 11-21.

Primary Examiner—F. L. Evans

[57] ABSTRACT

A fluorescence spectrometer comprises a light source with a flashlamp (2), means (9) for selecting an excitation wavelength, a sample cuvette (11), means (16) for spectrally separating the radiation emitted from the sample cuvette (11), and detector means (18) for detecting the spectrally separated radiation. The detector means (18) comprise an avalanche photodiode, preferably an array of avalanche photodiodes. The use of a flashlamp in combination with avalanche photodiodes ensures high sensitivity in the determination of low sample concentrations, in particular when the sample composition changes over time as in liquid chromatography.

11 Claims, 5 Drawing Sheets

FLUORESCENCE SPECTROMETER

This application is a continuation-in-part of application Ser. No. 08/390,853 filed Feb. 17, 1995, now abandoned.

The invention relates to a fluorescence spectrometer for analyzing a sample by measuring the fluorescence light emitted from the sample.

BACKGROUND OF THE INVENTION

In a fluorescence spectrometer, the sample to be analyzed is irradiated by excitation light which causes the sample to emit fluorescence light at characteristic wavelengths. The fluorescence light is measured by a suitable detector to derive information about the sample, in particular the composition of the sample and the quantities of the individual components present in the sample. Typically, the wavelength of the excitation light is adjusted by an optical component, such as a diffraction grating or a filter. The fluorescence light emitted is usually analyzed by a second diffraction grating or by a filter. For performing a fluorescence measurement, the grating at the excitation side of the spectrometer is set to a fixed excitation wavelength and the wavelength spectrum of the fluorescence light is recorded by means of the grating at the emission side (emission grating). The emission spectrum can be recorded for a plurality of excitation wavelengths. As an alternative thereto, the emission wavelength can be kept fixed and the excitation wavelength can be varied by corresponding adjustment of the excitation grating.

Because of the low intensities of the fluorescence light, most fluorescence spectrophotometers use a photomultiplier tube for detecting the light diffracted by the emission grating. When the fluorescence spectrophotometer is used for detecting the sample substances in liquid chromatography, it is still more important to use a detector which is able to detect low light intensities, because the sample stays within the area of the detector only for a short time. That means that common noise reduction techniques by increasing the integration time cannot be employed because the integration times in liquid chromatography are typically smaller than 100 milliseconds. Photomultiplier tubes are not satisfactory in all respects because of their relatively low quantum efficiency, their restricted linearity, because they are sensitive to magnetic fields and because they are bulky. Instead of a photomultiplier tube, a multi-channel plate might be used as a detector, but such a device is very costly and has similar limitations as a photomultiplier tube. Furthermore, the use of a photomultiplier tube has the disadvantage that the recording of an emission spectrum requires that the emission grating is mechanically rotated so that, depending on the angular position of the grating, different wavelengths impinge on the photomultiplier. Such mechanical rotation requires movable parts which lead to an increased complexity of the device which make it susceptible to faults. Additionally, mechanical rotation of the grating is slow. Particularly in time resolved measuring techniques like in liquid chromatography, where the composition of the sample to be analyzed quickly varies, the time for moving the grating is too long for recording the complete spectrum of a specific sample component. It is thus desirable to record the different wavelengths of the emission spectrum simultaneously, for example with an array of photosensitive detectors.

A fluorescence detector using a photodiode array is known from an article by J. Wegrzyn et al: "Unintensified Photodiode Array Fluorescence Detector for High-Performance Liquid Chromatography", Anal. Chem. 1990, 62, pages 1754–1758. In many trace analysis applications, however, such a photodiode array cannot provide the required sensitivity level. For example, the detection limit for anthracene of the known detector with a cooled photodiode array is 4.9 nanograms per 20 microliters, whereas in current trace analysis it is necessary to achieve a more than ten thousand times better detection limit.

SUMMARY OF THE INVENTION

In view of the prior art, it is thus an object of the present invention to create a fluorescence spectrometer having an improved sensitivity level.

It is a further object of the invention to provide a fluorescence spectrometer having an increased light throughput.

It is still a further object to provide a fluorescence spectrometer which allows the simultaneous recording of the different wavelength ranges of the fluorescence spectrum of the sample at low concentrations of the sample with high sensitivity.

It is a further object to provide simultaneous wavelength information in order to save time and costs which would otherwise be caused by multiple analyses of the same sample.

Another object is to provide a fluorescence spectrometer with high sensitivity and low cost.

According to the invention, these objects are solved by including a light source having a flashlamp, a sample cuvette, a detector including an avalanche photodiode, and an optical path between the light source and the avalanche photodiode via the sample cuvette. The optical path consists essentially of a non-solid medium between the flashlamp and the photodiode and has a first portion between the light source and the cuvette, as well as a second portion between the cuvette and the avalanche photodiode. The first portion includes: (i) a selector for an excitation wavelength of the source that is incident on a sample in the cuvette and (ii) first discrete optical elements. The selector and the first discrete optical elements are arranged for focusing the selected wavelength on the sample. The second portion includes: (i) a spectral separator for radiation emitted from the sample in the cuvette in response to the selected excitation wavelength that is incident on the sample and (ii) second discrete optical elements. The separator and the second discrete optical elements are arranged for imaging the spectrally separated radiation onto the avalanche photodiode. Because the optical path consists essentially of a non-solid medium between the flashlamp and the photodiode, the device of the present invention has much greater sensitivity than prior art fiber optic based systems and can be used, inter alia, with low intensity fluorescent samples, such as liquids moving through a liquid chromatograph.

The invention is based on our realization that a substantial improvement in the performance of a fluorescence spectrometer can be achieved by the use of avalanche photodiodes for detecting the fluorescence radiation emitted by the sample. The use of avalanche photodiodes permits the measurement of low light levels without requiring complex and costly detectors such as photomultiplier tubes. Furthermore, avalanche photodiodes can be manufactured as an array of several photodiodes arranged on a single semiconductor chip. With such an array of photodiodes, simultaneous detection of several wavelengths is possible, so that a fluorescence emission spectrum can be recorded in a very short time interval without requiring movable parts. The fast recording of a spectrum is particularly important in applications where the sample composition quickly varies with time, for example in liquid chromatography. Additional advantages of avalanche photodiodes relative to conventional detectors are their compact size, particularly in comparison to a photomultiplier tube, and the possibility to manufacture them with a large light-sensitive area. A large light-sensitive area is important for collecting as much fluorescence light as possible (together with a monochromator) and thus improving the signal-to-noise ratio. Preferred values for the entire light-sensitive area of the detector are 20 mm$^2$ and larger. A large light-sensitive area also ensures an optimum optical match to typical cuvette cross section areas between 1 to 2 mm width and 4 to 10 mm height.

According to another advantage of the invention, it has turned out that the detection limits which can be achieved with avalanche photodiodes in the range above approximately 450 nm can be up to 20 times better than with photomultipliers. The invention does therefore open up new areas for the application of fluorescence measurements, which were not accessible with prior art devices, Relative to photomultiplier tubes, the use of avalanche photodiodes has the advantage that they are not sensitive to magnetic fields, are rugged and compact, have a higher dynamic range and linearity.

In a preferred embodiment of the invention, the light-throughput from the light source to the sample cuvette and from the sample cuvette and consequently the signal-to-noise ratio is further improved by several special measures. In particular, the F/#-numbers of the optical components of the spectrometer are matched and selected very small. Typical values for the F/#-number of the means for selecting an excitation wavelength and the means for spectrally separating the radiation emitted from the sample cuvette are in the order of F/2 or smaller. A more detailed definition of F/#-number will be provided in the detailed description of the invention. Furthermore, it is preferred that an optical arrangement, such as lenses, is provided between the light source and the cuvette and/or between the cuvette and the detector means which provides an optical magnification.

The flashlamp used as the light source preferably is a bulb-type lamp, that means that the spot from which the radiation emerges is compact. This also contributes to a maximized light throughput in the spectrometer. It ensures optimum optical match to the cuvette cross-section and a short acquisition time for eliminating dark current noise of avalanche photodiodes.

The sample cuvette in a preferred embodiment of the invention as well as the apertures for shaping the excitation light beam entering the cuvette are designed such that a maximum illumination of the cuvette is achieved without cutting of the light beam. Preferably, the cuvette has the shape of a parallelepiped, that means that its cross-sections in two perpendicular planes are rectangles of different dimensions. Such a parallelepiped is particularly advantageous when the slit widths on the excitation and emission side are equal or similar and a magnifying optical system is used on the emission side.

According to a practical example of the invention, anthracene in a continuous flow of methanol has been detected at an excitation wavelength of 250 nm and at an emission wavelength of 400 nm. Compared to conventional fluorescence spectrometers, at least a four-fold improvement of the detection limit is achieved.

BRIEF DESCRIPTION OF THE DRAWINGS

Subsequently, an embodiment of the invention will be explained in detail with reference to the drawings.

FIG. 3b shows a magnified detail of FIG. 3a.

FIG. 3c is a side view of the sample cuvette according to FIG. 3a.

DETAILED DESCRIPTION OF THE INVENTION

Before the actual description of an embodiment of the invention, the technical term F/#-number will be explained with reference to FIGS. 1a–1e. The optical system of the fluorescence spectrometer of the invention is designed for optimum light throughput. Higher light levels at the detector ensure higher sensitivity of the spectrometer. The F/#-number is a measure of the light throughput (integral intensity) of optical units. Small F/#-numbers correspond to large angles and high light throughput, and vice versa. The term F/#-number will be used in the explanation of the invention for describing the light throughput of the different optical units of the fluorescence spectrometer.

Figure 1A:
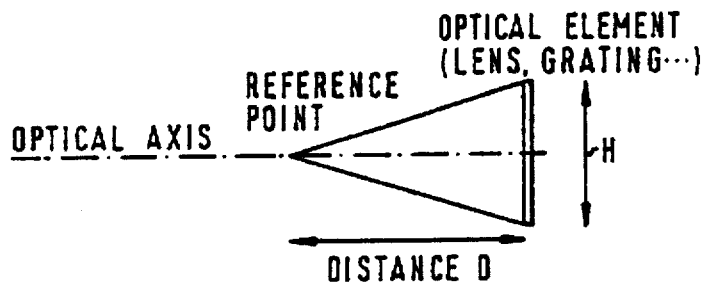
FIGS. 1a–1e schematically show optical imaging systems for the purpose of explaining the term F/#-number.
Figure 1B:
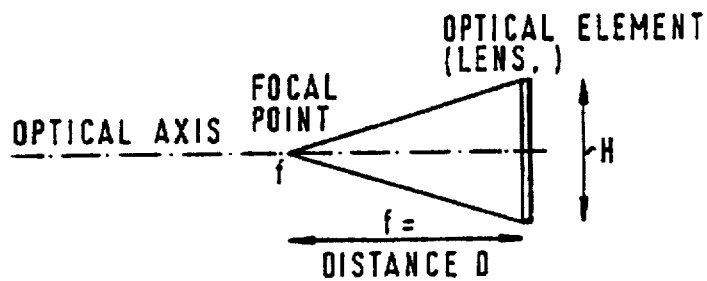
Figure 1C:
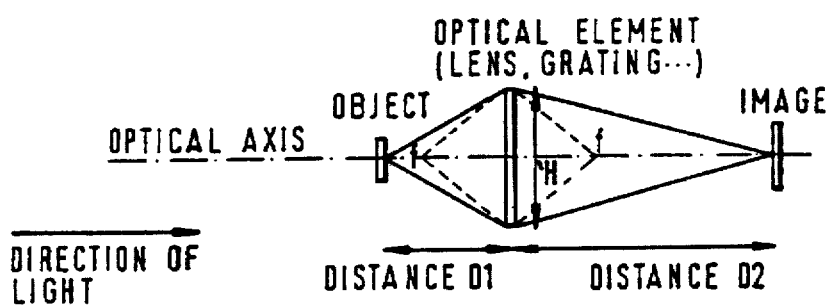

FIG. 1a illustrates the general meaning of the term F/#-number. It is the ratio of the distance D between a reference point and an optical element, for example a lens or a grating, and the height H (or diameter) of this optical element, i.e., F/#=D/H. A lens (or a grating) has a focal length f. This focal length f divided by the diameter of the lens gives the intrinsic F/#-number of the lens independent of the used image magnification (see FIG. 1b). The intrinsic F/#-number will be denoted as F/#(I). In an imaging system, which comprises an object, a lens, an image or entrance slit, a grating, and an exit slit, two further varieties of F/#-numbers are defined: a design nominal input and design nominal output F/#-number. These are often described as working design F/#-numbers, and are denoted as F/# (wd, input) and F/# (wd, output). FIG. 1c illustrates a typical imaging system. With H as the diameter of the optical element (lens or grating), with D1 as the distance between the object and the optical element and with D2 as the distance between the optical element and the image, the following relationships apply:

$$F/\# \text{ (wd, input)} = D1/H \text{ and } F/\# \text{ (wd, output)} = D2/H.$$

The working design F/#-number is independent of the object and image size. At a magnification of 1 it applies: F/# (wd, input)=F/# (wd, output). For monochromators, typically the working design F/#-number, i.e., F/# (wd), is used for the monochromator itself and also for the grating.

With consecutive imaging systems, there is a match between the first and the second system to a first approximation if the design output F/#-number, i.e., F/# (wd, output), of the first imaging system is nearly the same as the design input F/#-number, i.e., F/# (wd, input), of the second imaging system.

Figure 1D:
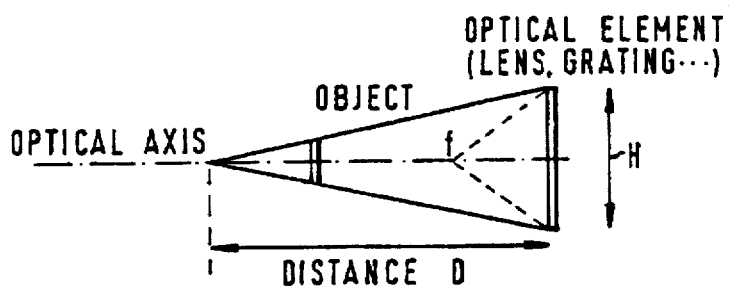
Figure 1E:
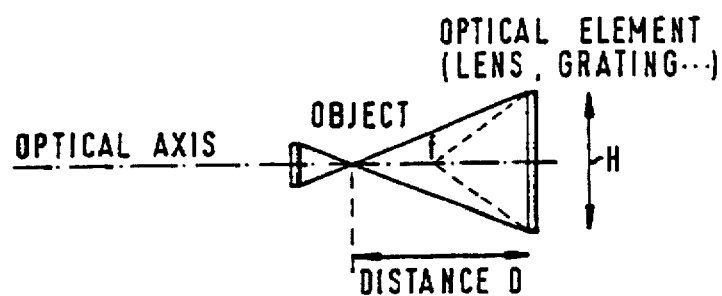

Finally, a "large" F/#-number, i.e., F/# (wl), and a "small" F/#-number, i.e., F/# (ws), are defined with reference to FIGS. 1d and 1e, respectively. In the cases illustrated in FIGS. 1d and 1e, the F/#-number is D/H, respectively. The use of the "large" and "small" F/#-numbers is of help for worst case light calculations. In order not to lose light, the following relationship must be valid:

F/# (ws,output) (system 1)>=F/# (wl,input) (system 2).

In the following description, the above defined abbreviated expressions will be used. When reference is made to a specific value of the F/#-number, the symbol "#" is replaced by the corresponding value.

Figure 2:
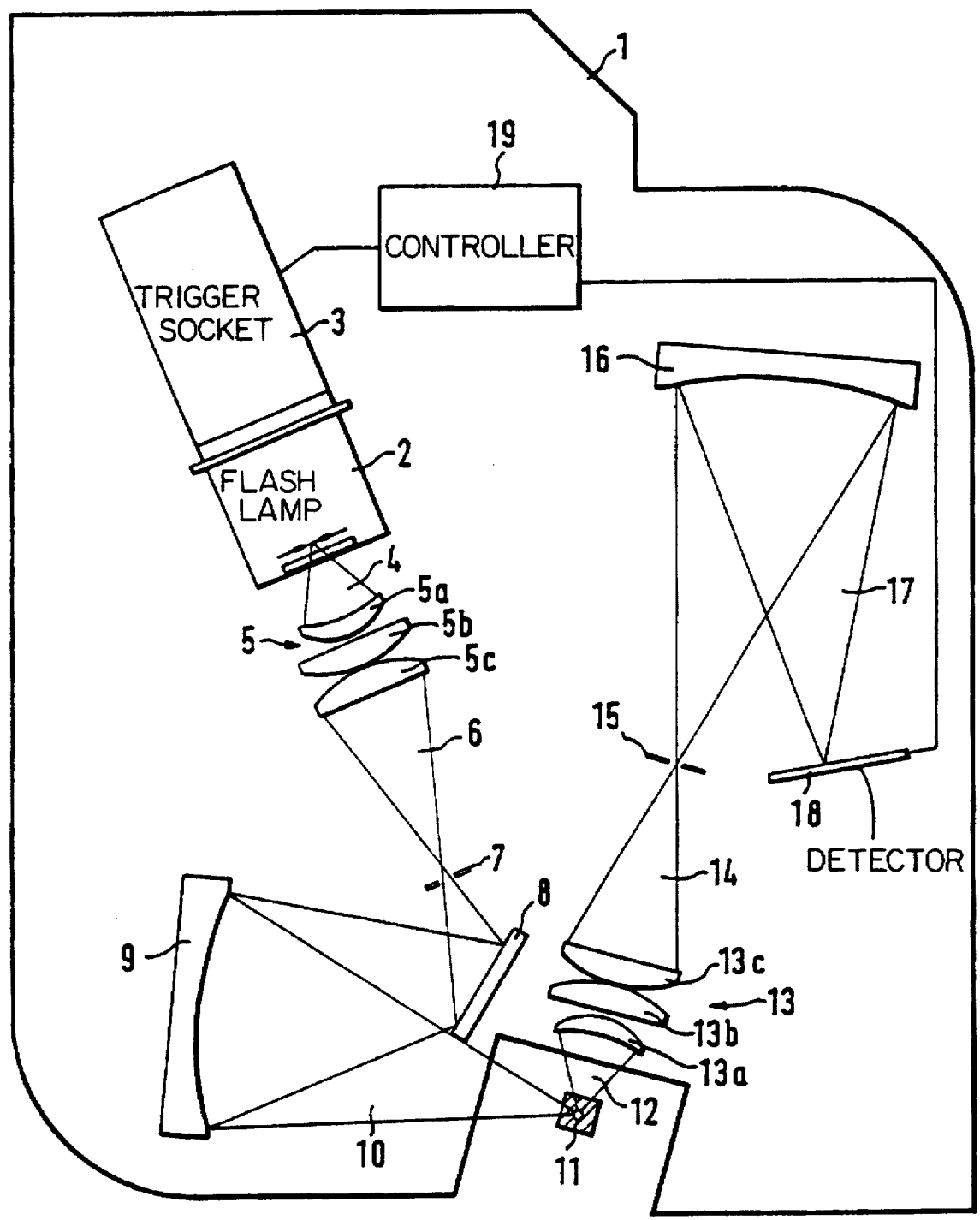
FIG. 2 is a schematic diagram of a fluorescence spectrometer according to an embodiment of the invention.

FIG. 2 is a schematic diagram of shows a fluorescence spectrometer according to an embodiment of the invention. The components of the spectrometer are arranged within a light-tight housing 1. The radiation for excitation of fluorescence light is provided by a flashlamp 2. Typically, a bulb-type Xenon flashlight is used. A trigger socket 3 connected to the flashlamp 2 comprises control electronics for controlling the operation of the flashlamp. Typical values of the flash frequency for this embodiment may lie, for example, in the range between 10 and 500 Hz. The equivalent peak power may range from about 50 to 1000 kW. For example, at a DC input of 20W, a flash frequency of 110 Hz and a flash time of 3 microseconds, the peak power of a flash is 60.6 kW. To analyze the specimens of greatest interest in cuvette 11 (i.e. polycyclical aromates (PAH), carbamates and amino acids), the current level applied to flashlamp 2 causes the flashlamp to emit optical energy in the ultraviolet range, between 250 and 350 nm. The flashlamp 2 preferably produces a high light intensity at a small plasma spot. This contributes, as will be explained in more detail below, to an increased light throughput through the spectrometer. In a practical example of this embodiment, the plasma spot has an area of about 1 mm×1.5 mm. A first optical path portion extending between flashlamp 2 and the sample in cuvette 11, consisting essentially of a non-solid medium including a gas or vacuum, as well as condenser lenses 5, slit plate 7, mirror 8 and wavelength selector grating 9, has, for the wavelength of lamp 2 selected by grating 9, a low attenuation factor of about twice that of an ideal non-attenuated path. Because of the low attenuation of this light path the optical energy of the wavelength selected by grating 9 incident on the specimen in cuvette 11 has sufficient energy to cause the sample to fluoresce, i.e. emit optical energy, over characteristic wavelengths in the 300–450 nm range.

The light cone 4 emitted by the flashlamp 2 impinges on a condenser 5 which converts the ingoing light cone 4 into a converging light cone 6. In the embodiment shown, the condenser 5 consists of three lenses 5a, 5b and 5c. The three lenses are preferably made of quartz so that light in the ultraviolet range can also be used for the excitation of fluorescence. According to a practical example of the invention, the optical components are selected such that the magnification factor of the imaging system is 2. A condenser with F/#(I)=F/0.64 is used. The preferred imaging system used has the following F/#-numbers:

F/# (wd, input)=F/0.96;

F/# (wd, output)=F/1.92 and

F/# (ws, output)=F/1.61

As an alternative to the three lenses 5a–5c, a single spherical or aspherical lens or a spherical or aspherical mirror could be used. While the preferred imaging system between lamp 2 and cuvette 11 has an F/#=F/1.6, imaging systems with smaller diameters and F/#s as high as F/4 can be employed to provide lower imaging energy between source 2 and cuvette 11 of about factor $6^3$ compared to an F/1.6 optical system. In addition, an inherent attenuation factor of 2 exists for all imaging systems caused by wavelength dependent transmission of the lens system and a grating diffraction efficiency.

The converging light beam 6 passes through an aperture 7 and impinges thereafter on a mirror 8. The purpose of the mirror 8 is to fold the beam path so that the optical system can be arranged in a space saving manner within the spectrometer housing 1. If the size of the spectrometer is not of importance, the mirror could be omitted. The beam reflected by the mirror 8 impinges on a focusing diffraction grating 9. The grating 9 is a concave holographic grating. It will also be referred to as the excitation grating. Like the condenser 5, the grating 9 has a small F/#-number. The F/#-number of this imaging system, called monochromator, is F/# (wd)=F/1.6, and it has a magnification of 1. This matches very closely to the F/# (ws, output) of the preceding imaging system.

The grating 9 directs a converging light beam 10 into a sample cuvette 11, preferably having square cross sections at right angles to the directions of incident beam 10 and emitted beam 13. The square cross section is preferred because it facilitates manufacture of the cuvette compared to other cuvette geometries. The wavelength of the beam 10, i.e., the excitation wavelength, can be adjusted by appropriate rotation of the excitation grating 9 around an axis perpendicular to the plane of the paper. The arrangement of the aperture 7, the grating 9, and the aperture 20 near the cuvette (see FIG. 3a) is called monochromator. The monochromator has a magnification factor of 1 and a working F/#-number of F/# (wd)=F/1.6.

The sample cuvette 11 contains the sample substances to be analyzed. Typically, the sample cuvette is a flow-through cuvette through which sample substances are continuously flowing. Such a flow-through cuvette can, for example, be connected to the outlet of the separation column of a liquid chromatograph from which the substances to be analyzed are eluting. The invention can of course also be used in general fluorescence spectroscopy where the sample to be analyzed is stagnant inside a microcuvette. The excitation light 10 entering the sample 11 excites the sample to emit fluorescence light. The fluorescence light 12 is observed at an angle of 90° with respect to the direction of the excitation light 10. The design of the cuvette 11 is such that a maximum volume inside the cuvette is illuminated by the excitation light and that as much of the fluorescence light emitted by the sample in the cuvette can be transmitted to a subsequent detector. Further details of the sample cuvette are explained below in connection with FIG. 3.

Optical energy emitted by the sample in cuvette 11 propagates via a second optical path portion to avalanche diode photodetector 18. The second optical path portion also consists essentially of a non-solid medium including a gas or vacuum, as well as condenser lenses 13, slit plate 15, and wavelength selector grating 16. The second optical path also has, for the wavelength emitted by the sample in cuvette 11 and selected by grating 16, a low attenuation factor of about twice that of an ideal non-attenuated path. The preferred imaging system has an F/#=F/0.64 which is a factor 25 times higher than the imaging energy of an F/#=F/4 imaging system. Because of the low attenuation of this optical path and the relatively high emission of the sample as a result of the low attenuation of the path between lamp 2 and cuvette 11 and because of the characteristics of avalanche photodiode detector 18, the avalanche photodiode detector generates a detectable current level above the photodiode dark current in response to the wavelength selected by grating 16 being incident on it. In particular, the cone of fluorescence light 12 impinges on a second condenser 13 which comprises three lenses 13a, 13b and 13c. In a practical example, the condenser 13 provides for a magnification of 2 and has F/#(1)=F/0.64. Instead of the arrangement with three lenses, a single aspherical lens or spherical lens or an aspherical or spherical mirror could also be used. The imaging system has the following working F/#-numbers:

F/# (wd,input)=F/0.96;

F/# (wd,output)=F/1.92; and

F/# (ws,output)=F/1.44

Preferably the attenuation, F/# and field of view of the first and second optical paths are about the same to facilitate manufacture and adjustment of the optical arrangement between lamp 2 and detector 18.

The beam 14 leaving the condenser 13 passes through a second aperture 15 and then impinges on a second diffraction grating 16. The grating 16 is a concave holographic flat field grating. The term "flat field" means that the spectral image plans of the grating is substantially flat. The grating 16 will also be denoted as emission grating. According to a practical example, the magnification factor of the emission grating 16 is 1, as is the magnification factor of the excitation grating 9.

The diffracted radiation leaving the emission grating 16 propagating toward light-sensitive avalanche photodiode detector 18 includes plural beams of different spatially separated wavelengths. In FIG. 2, only one of these beams 17 corresponding to a specific wavelength is shown. The diffracted beam 17 is focused on light-sensitive avalanche photodiode detector 18. A diffracted beam having a wavelength different from the beam 17 would impinge on the detector 18 at a position which is parallel shifted to the point of incidence of the beam 17, but its focus would also be at the detector 18. The entire spectrum of the beams of different wavelengths emitted by the grating 16 can be shifted across the detector 18 by corresponding rotation of the grating 16 around an axis perpendicular to the plane of the paper. The arrangement comprising the aperture 15 (i.e., "the entrance slit"), the grating 16 and the detector array 18 is called "spectrograph". The spectrograph of the preferred embodiment has F/# (wd)=F/1.6 i.e. it is the same as the F/# from aperture 7 to cuvette 11. However the spectrograph can have an F/# as high as F/4, which enables the required amount of optical energy to be incident on detector 18. If the F/# of the first or second optical path exceeds F/4 or the optical attenuation of the first and second light paths appreciably exceeds a factor of two, the amount of optical energy incident on avalanche photodiode detector 18 is likely to be insufficient to enable detector dark current to be exceeded for all wavelengths in the 300–450 nm wavelength range of primary interest.

According to an important aspect of the present invention, the light-sensitive detector 18 comprises one or several avalanche photodiodes. In the embodiment shown in FIG. 2, a linear array of a plurality of avalanche photodiodes is used as detector 18. The array of avalanche photodiodes is preferably manufactured from a single semiconductor chip. The advantage of an array of avalanche photodiodes relative to a single diode is that the entire emission spectrum can be recorded simultaneously since beams of different wavelengths impinge on different photodiodes. With a single photodiode, however, the grating 16 has to be rotated (or the photodiode has to be moved) to ensure that the detector detects beams of different wavelengths. The recording of an emission spectrum with ah array of photodiodes is thus less time-consuming and does not require a mechanical drive for the emission grating. Furthermore, if a single avalanche photodiode is used, an additional aperture has to be arranged in front of the diode to prevent deletion of beams having wavelengths other than that of interest. An additional advantage of an array as compared to a single diode is that no light is lost, having all the useful information for sample analysis is collected. Furthermore, the use of an array allows the signals measured by different photodiodes to be added together whereby the amount of collected light intensity and therefore the sensitivity can be improved.

Avalanche photodiodes have a substantially higher sensitivity; than conventional p-i-n photodiodes, so much lower light intensities can be detected. This is important in fluorescence measurements because the intensity of the fluorescence light is typically very small. Avalanche photodiodes internally multiply charge carriers (internal gain) so that the output signal is comparatively large even for very low light intensities. Avalanche photodiodes and avalanche photodiode arrays which could be used in a fluorescence spectrometer of the invention are available, for example, from Advanced Photonics, Inc., California. With such avalanche photodiodes, low light intensities can be detected better than with conventional photodiodes by a factor of up to 50. It has also turned out that, regarding sensitivity, avalanche photodiodes are superior to photomultiplier tubes which are presently used in most fluorescence spectrometers. In particular, in the spectral range above approximately 450 nm, the detection limits with avalanche photodiodes can be up to 20 times better than with photomultipliers. The invention does therefore open up new areas for the application of fluorescence measurements, where prior art devices did not give satisfactory results because of the mentioned limitations. We have found that the Advanced Photonics avalanche photodiode type 197-70-72-521 functions admirably to detect emissions in the 300–450 nm range even though this avalanche photodiode type is designed primarily to detect the visible spectrum, i.e., 400–700 nm. To enable detectable signal to be derived from the avalanche photodiode detector, the bias voltage applied between the photodiode anode and cathode must be selected as a function of diode dark current and photon gain for the wavelengths of the photons detected by the photodiode and emitted by the sample in cuvette 11.

Furthermore, avalanche photodiodes can be manufactured with a large light-sensitive area. A large light-sensitive area is important to ensure that as much fluorescence light as possible is detected so that high signal-to-noise ratio and high sensitivity are achieved. In the above described example of an optical system of the spectrometer of the invention, the plasma spot of the Xenon flashlight is 1.5 mm high and 1 mm wide, and the optical system generates a magnification of 4 (two times a magnification of 2) so that the avalanche photodiode or the photodiodes in case of an array should have a height of 4×1.5 mm=6 min. Typically, avalanche photodiodes with a light-sensitive area that is several millimeters high and wide are used. In a practical embodiment of the invention, an array of avalanche photodiodes is used wherein each individual light-sensitive diode has an area of 0.5 mm×6 min. The array has approximately 30 individual photodiodes. Further examples of large area avalanche photodiodes and avalanche photodiode arrays as such are described in U.S. Pat. No. 5,057,892 and U.S. Pat. No. 5,021,854.

When a fluorescence spectrum is recorded the light pulses of the flashlamp 2 and the measuring time interval of the detector 18 are synchronized. To synchronize controller 19 is connected to the trigger socket 3 of the flashlamp 2 and to the detector 18. The detector 18 is controlled so the avalanche photodiodes of detector 18 are read out only after the flashlamp 2 has emitted a light pulse. The controller 19 also controls other functions of the fluorescence spectrometer, such as the adjustment of different excitation wavelengths by rotating grating 9; if a single avalanche diode, instead of an array is used, controller 19 controls the movement of the emission grating 16 or of the avalanche diode.

The invention can be used advantageously in liquid chromatography for the quantitative determination of the sample substances which are consecutively leaving the separation column. Since sample substances are constantly eluting from the separation column, the sample just passes through the sample cuvette without staying there for longer. The fluorescence measurement of a sample substance therefore has to be completed within a short time interval. Due to this limited measuring time, the amount of fluorescence light which can be detected is reduced and is likely to be relatively low. With the highly sensitive avalanche photodiodes according to the invention, however, meaningful measurements can still be made. When an array of avalanche photodiodes is used as the detector, it is even possible to record a wavelength spectrum of the sample substances as the sample is moving through the sample cuvette.

In the following, an embodiment of the sample cuvette (reference numeral 11 in FIG. 2) and the components associated therewith are described in more detail with reference to FIGS. 3a, 3b, 3c, and 3d.

Figure 3A:
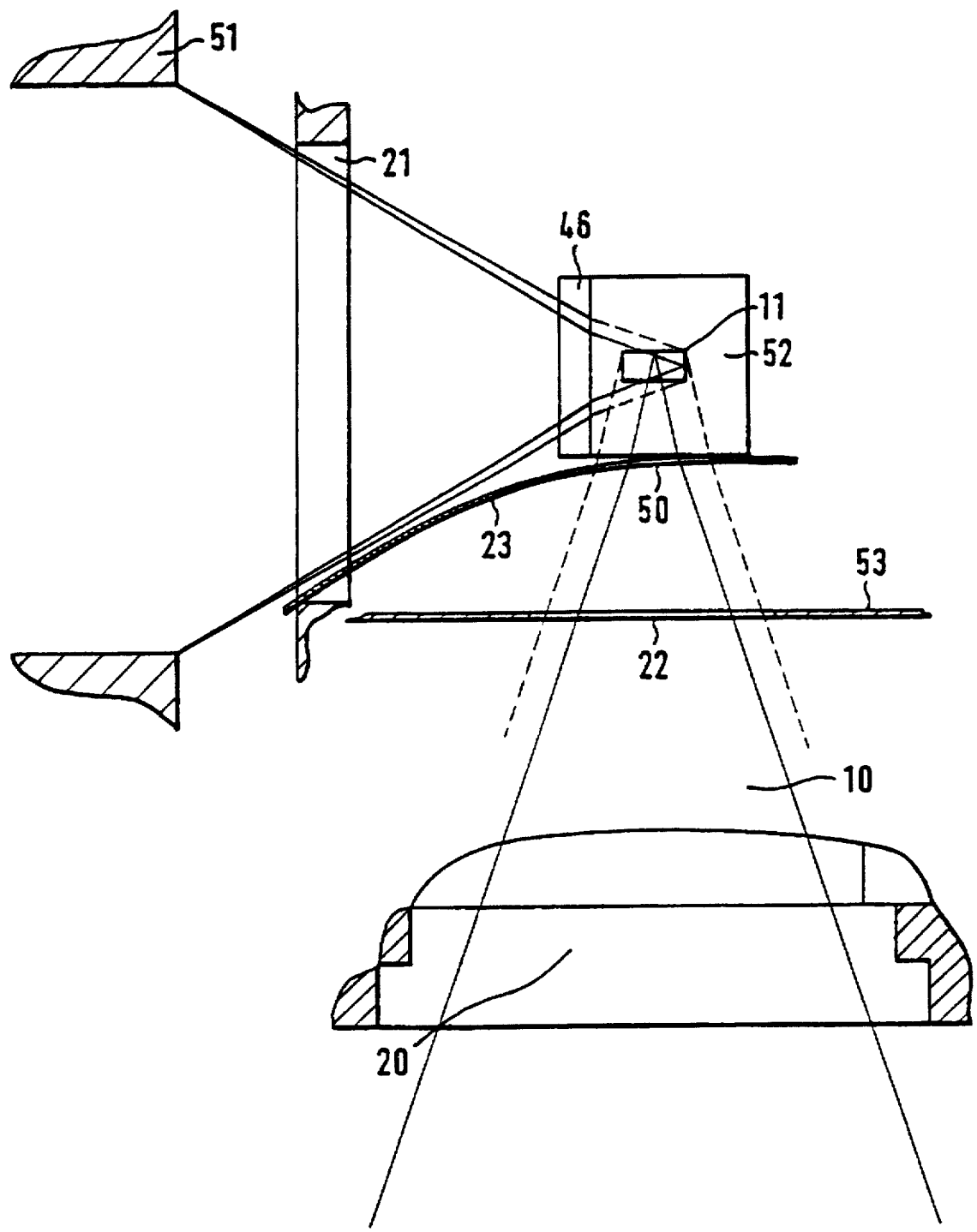
FIG. 3a is a top view of the sample cuvette and surrounding optical components in a fluorescence spectrometer of the invention.

FIG. 3a is a top view of the sample cuvette 11 and of the surrounding optical components. Reference numerals 20 and 22 denote apertures through which excitation light 10 is directed into the sample cuvette 11. Reference numeral 23 denotes a member having an opening 50 for the passage of the beam 10 and an opaque portion (curved, at the left) which prevents that excitation light for reaching the emission side. The member 23 typically is made of, for example, a flexible metal sheet. The sample cuvette 11 is designed as a cavity within a quartz block 52. The cavity has a rectangular cross-section. On the emission side, the quartz block 52 has a small recess with a chamfer 46. The chamfer ensures minimum cutting of the beam leaving the cuvette 11. The mentioned chamfer is described in a different section in connection with FIG. 3c. The fluorescence light leaves the sample cuvette at an angle of 90 degrees displaced from the light incident on the sample cuvette; the light leaving the cuvette passes through an aperture 21. The lens holder 51 of the following condenser is a further aperture of the optical system. The plate 53 in which the aperture 22 is defined and the member 23 are very thin (typically 0.08 and 0.2 mm thickness) in order to avoid scattering surfaces which are parallel to the optical axis. In that way, the excitation light does not reach the emission beam.

Figure 3B:
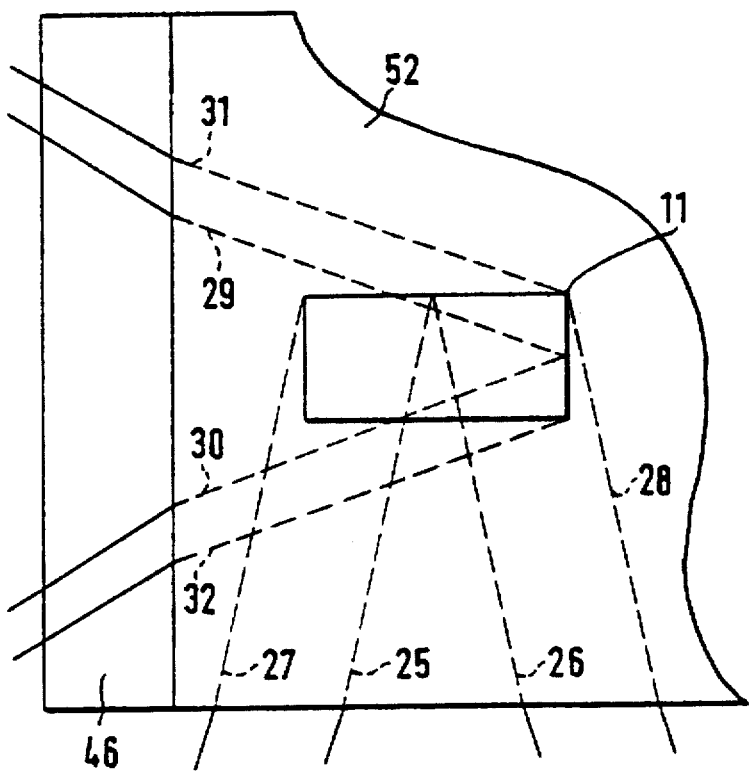

FIG. 3b corresponds to the same view as FIG. 3a; in FIG. 3b some of the light rays entering and leaving the sample cuvette 11 are shown as propagating through the quartz block 52. The rays 25 and 26 are the center rays of the excitation beam, and rays 27 and 28 are the marginal rays of the excitation beam. On the emission side of the cuvette 11, there are the center rays 29 and 30 as well as the marginal rays 31 and 32. As can be seen in FIG. 3b, the dimensions of the optical components are selected such that there are no limitations in the illumination of the sample cuvette from the excitation and emission point of view. Combined with the mentioned measures to prevent excitation light from reaching the emission light beam, maximum light throughput and minimization of stray-light are ensured.

Figure 3D:
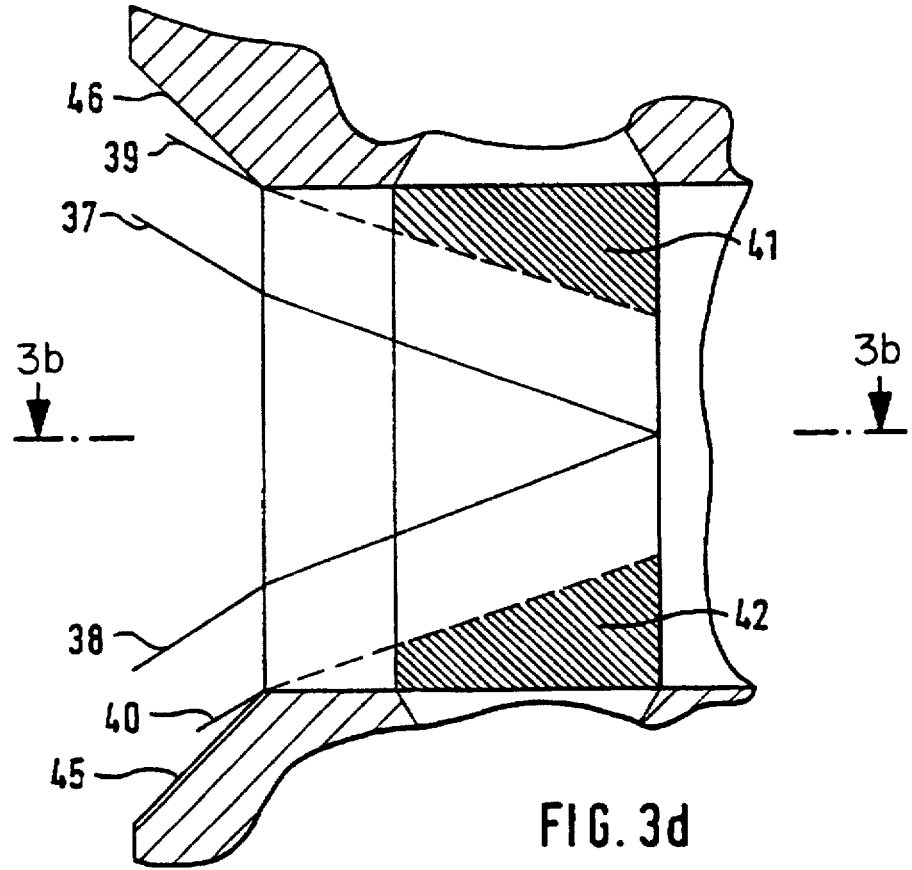
FIG. 3d shows a magnified detail of FIG. 3c.
Figure 3C:
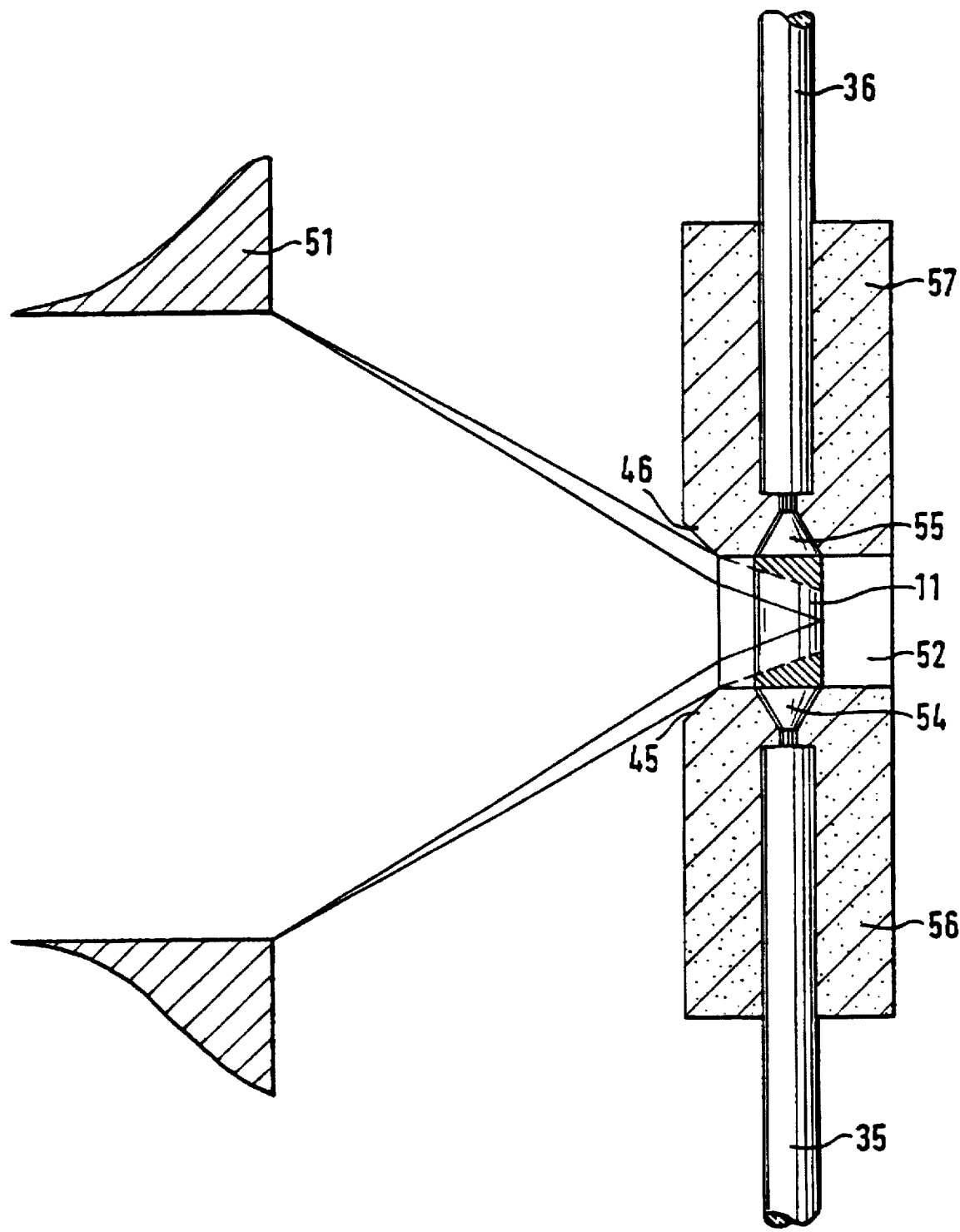

FIG. 3c is a side view of the sample cuvette 11. Adjacent to the quartz block 52 are two blackened quartz blocks 56 and 57, respectively including an inlet capillary 35 and an outlet capillary 36. According to an embodiment of the invention, the blocks 52, 56 and 57 are manufactured from a common piece. The sample to be analyzed enters the cuvette 11 through the inlet capillary 35 and an inlet channel 54 in the blackened block 56 and leaves the cuvette through an outlet channel 55 in the block 57 and an outlet capillary 36. FIG. 3d is a magnified detail of FIG. 3c. The rays 37 and 38 are the center rays of the emission beam which are directed towards the grating 16. Regions rays 39 and 40 are the marginal rays of the emission beam. The areas 41 and 42 are of reduced light throughput (vignetting) which are caused by the cuvette holder, or by any cuvette seals, if present, or by other beam limitations. In the present example, the vignetting is reduced to a minimum due to the provision of the 45 degree chamfers 45 and 46 in the blackened quartz blocks 56 and 57. As is apparent from FIGS. 3b and 3d, the sample cuvette 11 has the shape of a parallelepiped, that means that the cross-section in each of the two planes perpendicular to beams 10 and 12 is a rectangle and is preferably square, as discussed supra. FIG. 3b corresponds to a section along the line 3b—3b in FIG. 3d. The mentioned shape of the cuvette contributes to an optimized light throughput.

In a practical example, the angle between the rays 29 and 30 as well as the angle between the rays 37 and 38, both at the emission side of the sample cuvette, is approximately 65 degrees. Due to these large angles, a maximum of fluorescence light is collected by the subsequent detector. The angle between the rays 25 and 26 at the excitation side is approximately 35 degrees. This angle ensures that a maximum amount of excitation light reaches the cuvette 11. Hence, the F/# and field of view angle of the optical system including discrete lenses 5, aperture 7 and discrete mirror 8 in the first optical path portion from flash lamp 2 to cuvette 11 and in the second optical path portion including discrete lenses 13 and aperture 15 between cuvette 11 and detector 18 are respectively much lower and much wider than the F/# and field of view of a fiber optical path between a flash lamp and cuvette. Fiber optic optical paths typically have high F/#s of about F/11 and narrow field of view angles of about 5°. The preferred imaging system works with F/#=F/0.64 which is equivalent to an F factor 200 times the optical energy that would have been collected by an F/11 fiber optic system. Hence, the amount of optical energy incident on a photocell of the preferred imaging system is about 200 times greater than the amount of optical energy incident on a photocell responsive to light from the F/11 fiber optic system.

We claim:
1. A fluorescence spectrometer comprising
   a light source including a flashlamp,
   a sample cuvette,
   a detector including an avalanche photodiode,
   an optical path consisting essentially of a non-solid medium between the light source and the avalanche photodiode via the sample cuvette,
   the optical path including a first portion between the light source and the cuvette and a second portion between the cuvette and the avalanche photodiode, the first portion including: (i) a selector for an excitation wavelength of the source to be incident on a sample in the cuvette and (ii) first discrete optical elements, the selector and the first discrete optical elements being arranged for focusing the selected wavelength on the sample; the second portion including: (i) a spectral separator for radiation emitted from the sample in the cuvette in response to the selected excitation wave- length that is incident on the sample and (ii) second discrete optical elements, the separator and the second discrete optical elements being arranged for imaging the spectrally separated radiation onto the avalanche photodiode, the avalanche photodiode having a detection area greater than approximately 20 mm$^2$.

2. A fluorescence spectrometer comprising a light source including a flashlamp, a sample cuvette, a detector including an avalanche photodiode, an optical path consisting essentially of a non-solid medium between the light source and the avalanche photodiode via the sample cuvette, the optical path including a first portion between the light source and the cuvette and a second portion between the cuvette and the avalanche photodiode, the first portion including: (i) a selector for an excitation wavelength of the source to be incident on a sample in the cuvette and (ii) first discrete optical elements, the selector and the first discrete optical elements being arranged for focusing the selected wavelength on the sample; the second portion including: (i) a spectral separator for radiation emitted from the sample in the cuvette in response to the selected excitation wavelength that is incident on the sample and (ii) second discrete optical elements, the separator and the second discrete optical elements being arranged for imaging the spectrally separated radiation onto the avalanche photodiode, the avalanche photodiode being one of many avalanche photodiodes of an array, the avalanche photodiodes of the array being arranged so different photodiodes of the array have different portions of the spectrum of the spectrally separated radiation simultaneously incident thereon, the total detection area of the avalanche photodiodes being larger than approximately 20 mm$^2$ and the area of the individual avalanche photodiodes being larger than approximately 1 mm$^2$.

3. A fluorescence spectrometer comprising a light source including a flashlamp, a sample cuvette, a detector including an avalanche photodiode, an optical path consisting essentially of a non-solid medium between the light source and the avalanche photodiode via the sample cuvette, the optical path including a first portion between the light source and the cuvette and a second portion between the cuvette and the avalanche photodiode, the first portion including: (i) a selector for an excitation wavelength of the source to be incident on a sample in the cuvette and (ii) first discrete optical elements, the selector and the first discrete optical elements being arranged for focusing the selected wavelength on the sample; the second portion including: (i) a spectral separator for radiation emitted from the sample in the cuvette in response to the selected excitation wavelength that is incident on the sample and (ii) second discrete optical elements, the separator and the second discrete optical elements being arranged for imaging the spectrally separated radiation onto the avalanche photodiode, the spectral separator for the radiation emitted from the sample cuvette having a working F/#-number (F/# (wd)) of approximately F/2 or smaller.

4. A fluorescence spectrometer comprising a light source including a flashlamp, a sample cuvette, a detector including an avalanche photodiode, an optical path consisting essentially of a non-solid medium between the light source and the avalanche photodiode via the sample cuvette, the optical path including a first portion between the light source and the cuvette and a second portion between the cuvette and the avalanche photodiode, the first portion including: (i) a selector for an excitation wavelength of the source to be incident on a sample in the cuvette and (ii) first discrete optical elements, the selector and the first discrete optical elements being arranged for focusing the selected wavelength on the sample; the second portion including: (i) a spectral separator for radiation emitted from the sample in the cuvette in response to the selected excitation wavelength that is incident on the sample and (ii) second discrete optical elements, the separator and the second discrete optical elements being arranged for imaging the spectrally separated radiation onto the avalanche photodiode, each of the first optical path portion and the second optical path portion having an attenuation factor of about two relative to an ideal non-attenuated optical path.

5. A fluorescence spectrometer comprising a light source including a flashlamp, a sample cuvette, a detector including an avalanche photodiode, an optical path consisting essentially of a non-solid medium between the light source and the avalanche photodiode via the sample cuvette, the optical path including a first portion between the light source and the cuvette and a second portion between the cuvette and the avalanche photodiode, the first portion including: (i) a selector for an excitation wavelength of the source to be incident on a sample in the cuvette and (ii) first discrete optical elements, the selector and the first discrete optical elements being arranged for focusing the selected wavelength on the sample; the second portion including: (i) a spectral separator for radiation emitted from the sample in the cuvette in response to the selected excitation wavelength that is incident on the sample and (ii) second discrete optical elements, the separator and the second discrete optical elements being arranged for imaging the spectrally separated radiation onto the avalanche photodiode, each of the first optical path portion and the second optical path portion having about the same F/#, the F/# being no greater than F/4.

6. A method of detecting fluorescence properties of a sample with a fluorescence spectrometer, comprising the steps of:

irradiating and exciting the sample with a selected first optical energy wavelength emitted by a flashlamp and propagating from the flashlamp to the sample via a first optical path portion consisting essentially of a non-solid medium, the first optical path portion focusing the selected first wavelength on the sample, the selected first wavelength having sufficient intensity when incident on the sample to cause the sample to emit optical energy in a predetermined wavelength range, and imaging a selected second wavelength of the optical energy emitted by the sample in the predetermined wavelength range on an avalanche photodiode detector, detecting the selected second wavelength with the avalanche photodiode, the selected second wavelength propagating from the sample to the avalanche photodiode via a second optical path portion consisting essentially of a non-solid medium, the second wavelength having sufficient intensity when incident on the avalanche photodiode detector to cause the photodiode to emit a detectable current level above the photodiode dark current, and detecting the detectable current level, both of the optical path portions having an attenuation of no less than about twice that of an ideal non-attenuated path.

7. The method of claim 6 wherein both of the optical path portions have lenses to provide a magnification factor of greater than 1.

8. The method of claim 7 wherein the flashlamp produces a peak power in the range from about 50 kW to 1000 kW on a substantially rectangular area of the sample having dimensions of about 1 mm×1.5 mm.

9. A method of detecting fluorescence properties of a sample with a fluorescence spectrometer, comprising the steps of:

irradiating and exciting the sample with a selected first optical energy wavelength emitted by a flashlamp and propagating from the flashlamp to the sample via a first optical path portion consisting essentially of a non-solid medium, the first optical path portion focusing the selected first wavelength on the sample, the selected first wavelength having sufficient intensity when incident on the sample to cause the sample to emit optical energy in a predetermined wavelength range, and imaging a selected second wavelength of the optical energy emitted by the sample in the predetermined wavelength range on an avalanche photodiode detector, detecting the selected second wavelength with the avalanche photodiode, the selected second wavelength propagating from the sample to the avalanche photodiode via a second optical path portion consisting essentially of a non-solid medium, the second wavelength having sufficient intensity when incident on the avalanche photodiode detector to cause the photodiode to emit a detectable current level above the photodiode dark current, and detecting the detectable current level, the sample being selected from the group consisting essentially of polycyclical aromates, carbamates and amino acids, and the selected first optical energy wavelength is in the 250–350 nm range and the second optical energy wavelength is in the 300–450 nm range.

10. A method of detecting fluorescence properties of a sample with a fluorescence spectrometer, comprising the steps of:

irradiating and exciting the sample with a selected first optical energy wavelength emitted by a flashlamp and propagating from the flashlamp to the sample via a first optical path portion consisting essentially of a non-solid medium, the first optical path portion focusing the selected first wavelength on the sample, the selected first wavelength having sufficient intensity when incident on the sample to cause the sample to emit optical energy in a predetermined wavelength range, and imaging a selected second wavelength of the optical energy emitted by the sample in the predetermined wavelength range on an avalanche photodiode detector, detecting the selected second wavelength with the avalanche photodiode, the selected second wavelength propagating from the sample to the avalanche photodiode via a second optical path portion consisting essentially of a non-solid medium, the second wavelength having sufficient intensity when incident on the avalanche photodiode detector to cause the photodiode to emit a detectable current level above the photodiode dark current, and detecting the detectable current level, both of the optical path portions having an F/# less than F/4.

11. The method of claim 10 wherein both of the optical path portions have approximately the same F/#.

* * * * *